(12) United States Patent
Mukkamala (10) Patent No.: US 8,282,569 B2
(45) Date of Patent: Oct. 9, 2012

(54) METHOD AND APPARATUS FOR DETERMINING EJECTION FRACTION

(75) Inventor: Ramakrishna Mukkamala, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1025 days.

(21) Appl. No.: 12/225,133

(22) PCT Filed: Mar. 15, 2007

(86) PCT No.: PCT/US2007/006454
§ 371 (c)(1),
(2), (4) Date: Sep. 15, 2008

(87) PCT Pub. No.: WO2007/109059
PCT Pub. Date: Sep. 27, 2007

(65) Prior Publication Data

US 2009/0112113 A1    Apr. 30, 2009

Related U.S. Application Data (60) Provisional application No. 60/782,724, filed on Mar. 15, 2006.

(51) Int. Cl.
*A61B 5/021* (2006.01)
*A61B 5/026* (2006.01)

(52) U.S. Cl. .................. 600/526; 600/301; 600/485

(58) Field of Classification Search .............. 600/485, 600/301, 526
See application file for complete search history.

(56) References Cited

U.S. PATENT DOCUMENTS

| 5,086,776 A | 2/1992 | Fowler, Jr. | |
| 5,450,850 A | 9/1995 | Iinuma | |
| 6,090,047 A * | 7/2000 | Kass et al. | 600/485 |
| 6,520,917 B1 | 2/2003 | Kunig | |
| 2003/0109772 A1 | 6/2003 | Mills | |
| 2004/0158163 A1 * | 8/2004 | Cohen et al. | 600/508 |
| 2005/0187481 A1 | 8/2005 | Hatib et al. | |

OTHER PUBLICATIONS

Segers P et al: "Predicting systolic and diastolic aortic blood pressure and stroke volume in the intact sheep" Journal of Biomechanics Elsevier UK, vol. 34, No. 1, Jan. 2001, pp. 41-50, XP002489273, ISSN: 0021-9290, paragraphs [02.1]—[02.7].

Elie H. Karam, Antoine B. Abche: "Left ventricular model using second order electromechanical coupling: effects of viscoelastic damping" Proceedings of World Academy of Science, Engineering and Technology, vol. 11, Feb. 2006, pp. 290-295, XP002489274, ISSN: 1307-6884, paragraph [00II].

Edward Marcus, Damien Craig, Ira Cheifetz: "Models of right ventricular shape and function" Inter Journal, Complex Systems, 2004, XP002489275, ISSN: 1081-0625, the whole document.

(Continued)

*Primary Examiner* — Tammie K Heller
(74) *Attorney, Agent, or Firm* — Harness, Dickey & Pierce, P.L.C.

(57) ABSTRACT

A method is provided for determining ejection fraction. The method includes: measuring a physiologic signal indicative of blood pressure; analyzing the physiologic signal at more than one time instance so as to extract information present in its temporal variations; and determining ejection fraction based in part on the extracted information.

57 Claims, 5 Drawing Sheets

OTHER PUBLICATIONS

Mukkamala R et al: "Continuous cardiac output monitoring by peripheral blood pressure waveform analysis" IEEE Transactions on Biomedical Engineering IEEE USA, vol. 53, No. 3, Mar. 1, 2006, pp. 459-467, XP002489276, ISSN: 0018-9294, col. 2, p. 459-p. 462.

Thomas Heldt, Eun B. Shim, Roger D. Kamm, Rober G. Mark: "Computational modeling of cardiovascular response to orthostatic stress" Journal of applied Physiology, vol. 92, 2002, pp. 1239-1254, XP002489277, ISSN: 8750-7587, p. 1241, col. 1.

* cited by examiner

METHOD AND APPARATUS FOR DETERMINING EJECTION FRACTION

CROSS-REFERENCE TO RELATED APPLICATIONS

This application is a 371 U.S. National Stage of International Application No. PCT/US2007/006454, filed Mar. 15, 2007 and published in English as WO 2007/109059 A2 on Sep. 27, 2007. This application claims the benefit of U. S. Provisional Application No. 60/782,724, filed Mar. 15, 2006. The disclosures of the above applications are incorporated herein by reference.

FIELD

The present disclosure relates to a technique for determining ejection fraction.

BACKGROUND

Ejection fraction (EF) is defined as the ratio of the stroke volume (SV) to the ventricular end-diastolic volume (EDV) and is expressed in percent. More simply, EF represents the percentage of the total volume in a ventricular chamber that is ejected per beat. EF is perhaps the most clinically significant index of global ventricular function. For example, epidemiological data have shown a powerful curvilinear relationship between left ventricular (LV) EF and outcome in patients with heart failure. As another example, a reduced LVEF has recently been recommended as the single factor for determining which post-myocardial infarction (heart attack) patients should be implanted with a potentially life-saving, but expensive, defibrillator. Thus, methods and apparatus for effectively monitoring EF are extremely desirable in that they would greatly facilitate the monitoring, diagnosis, and treatment of cardiovascular disease.

Several methods have been developed for measuring EF or ventricular volume. Note that EF may be trivially computed from the ventricular EDV and end-systolic volume (ESV) as follows:

$$EF = \frac{SV}{EDV} = \frac{EDV - ESV}{EDV}. \quad (1)$$

In clinical practice, EF is primarily determined by imaging the ventricular volume via echocardiography (transthoracic or transesophageal), radionuclide techniques (first pass or equilibrium), contrast angiography, ultra-fast computed tomography (CT), and magnetic resonance imaging (MRI). Each of these imaging methods offers some advantages and disadvantages with respect to each other in terms of, for example, the level of invasiveness, need for radiation exposure or contrast agents, and assumptions about ventricular geometry. However, imaging methods generally suffer from the major disadvantages of requiring an expert operator as well as bulky and expensive equipment. Thus, EF measurements can only be obtained in the clinical setting and are usually made few and far between (e.g., days to months).

To improve upon the significant disadvantages shared by imaging techniques, a few methods have been introduced for continuous and automatic monitoring of EF or ventricular volume. These methods include continuous thermodilution technique, the non-imaging nuclear monitor, the conductance catheter, and sonomicrometry. However, these methods are all limited in at least one clinically significant way.

The continuous thermodilution method involves automatic heating of blood in the right ventricle via a thermal filament, measurement of the temperature changes downstream in the pulmonary artery via a fast response thermistor, construction of a bolus thermodilution washout decay curve, and estimation of right ventricular (RV) EF based on the extent of the temperature decay over a cardiac cycle. An attractive feature of this method is that it requires only a pulmonary artery catheterization, which is routinely performed in a subset of critically ill patients (see below). As a result, the method is sometimes conducted in clinical practice, though it has yet to gain widespread popularity. On the other hand, the method does not provide beat-to-beat estimates of RVEF but rather estimates at time intervals of approximately a minute or more. Furthermore, the method continually perturbs the circulation and is not amenable to ambulatory or home health care monitoring, both of which could potentially reduce hospital admissions and health care costs. But, perhaps the most significant limitation of this method is that it cannot be utilized to determine the more clinically relevant LVEF.

In contrast, the non-imaging nuclear monitor, the conductance catheter, and sonomicrometry do permit automatic, beat-to-beat monitoring of LVEF. However, as discussed below, the substantial limitations of each of these methods have precluded their use in clinical practice.

In non-imaging nuclear monitoring of LVEF, the patient is given an injection of a radioactive tracer, which distributes throughout the circulation. The amount of the radioactive tracer in the LV is then measured with a crystal scintillation detector attached to a single bore converging collimator. The method is able to monitor LV volume at a high temporal resolution (10 ms) by sacrificing the spatial resolution, which would otherwise be needed to produce images. An appealing feature of the method is that LVEF is estimated without any assumptions about ventricular geometry. Additionally, systems have been developed for both bedside and ambulatory monitoring. However, the method is not in clinical use because of the difficulty in positioning the detector at the appropriate location on the patient's chest and in correcting for background radioactivity originating from extra-cardiac regions. The method also has the obvious disadvantage of exposing the patient to radiation.

The conductance catheter method involves placing a multi-electrode catheter in a ventricular cavity, continually applying AC current to the electrodes to generate an electric field, measuring the resulting voltage gradients, and estimating the ventricular volume from the intra-ventricular conductance using geometric assumptions. Thus, the method is able to provide estimates of either LVEF or RVEF. However, for LVEF, the method requires a left heart catheterization, which is rarely performed in critically ill patients. Moreover, the method is not capable of accurately estimating absolute or proportional ventricular volume, which is needed to reliably compute EF, due mainly to the parallel conductance (offset error) and non-uniformity of the generated electric field (scale factor error). Finally, another disadvantage of this method is that it is not amenable to ambulatory or home health care monitoring.

Sonomicrometry involves suturing crystals to opposite sides of the ventricular endocardium and using the ultrasound transit time principle to estimate the ventricular volume based on geometric assumptions. While the method can provide accurate estimates of either LVEF or RVEF when a sufficient number of crystals are used, it is obviously much too invasive to ever be employed in clinical practice.

It would be desirable to be able to accurately monitor beat-to-beat LVEF and beat-to-beat RVEF based on the mathematical analysis of continuous blood pressure. Continuous blood pressure is routinely monitored in clinical practice and several systems are currently available for continuous monitoring of specifically systemic arterial pressure (SAP, e.g., invasive catheters, non-invasive finger-cuff photoplethysmography, non-invasive arterial tonometry, and implanted devices), LV pressure (LVP, e.g., implanted devices), pulmonary artery pressure (PAP, e.g., invasive pulmonary artery catheters and implanted devices), and RVP (e.g., invasive pulmonary artery catheters and implanted devices). Thus, in contrast to the aforementioned methods, this approach would readily permit continuous and automatic measurement of LVEF and RVEF in the context of several important clinical applications. For example, such an approach could be applied to: 1) routinely employed invasive SAP and PAP catheter systems for titrating therapy in the intensive care unit (ICU), continuous monitoring of cardiac surgery in the operating room (OR), and remote ICU monitoring; 2) implanted SAP, PAP, and RVP systems for chronic, ambulatory monitoring of cardiovascular disease and facilitating the diagnosis of ischemia with surface ECGS; and 3) non-invasive SAP systems for emergency room (ER) or home health care monitoring. Note that these clinical applications of continuous and automatic EF monitoring have, for the most part, not been realized with the currently available measurement methods. Moreover, a blood pressure-based approach could estimate EF without making any assumptions about the ventricular geometry.

The statements in this section merely provide background information related to the present disclosure and may not constitute prior art

SUMMARY

A method is provided for determining ejection fraction. The method includes: measuring a physiologic signal indicative of blood pressure; analyzing the physiologic signal at more than one time instance so as to extract information present in its temporal variations; and determining ejection fraction based in part on the extracted information.

One exemplary embodiment of this method involves the use of a circulatory model to estimate the parameters used to compute ejection fraction. The method includes: measuring a physiologic signal; defining a circulatory model to predict the physiologic signal; estimating parameters of the circulatory model from the physiologic signal; and determining ejection fraction based on the estimated model parameters and the physiologic signal.

Further areas of applicability will become apparent from the description provided herein. It should be understood that the description and specific examples are intended for purposes of illustration only and are not intended to limit the scope of the present disclosure.

The drawings described herein are for illustration purposes only and are not intended to limit the scope of the present disclosure in any way.

DETAILED DESCRIPTION

Figure 1:
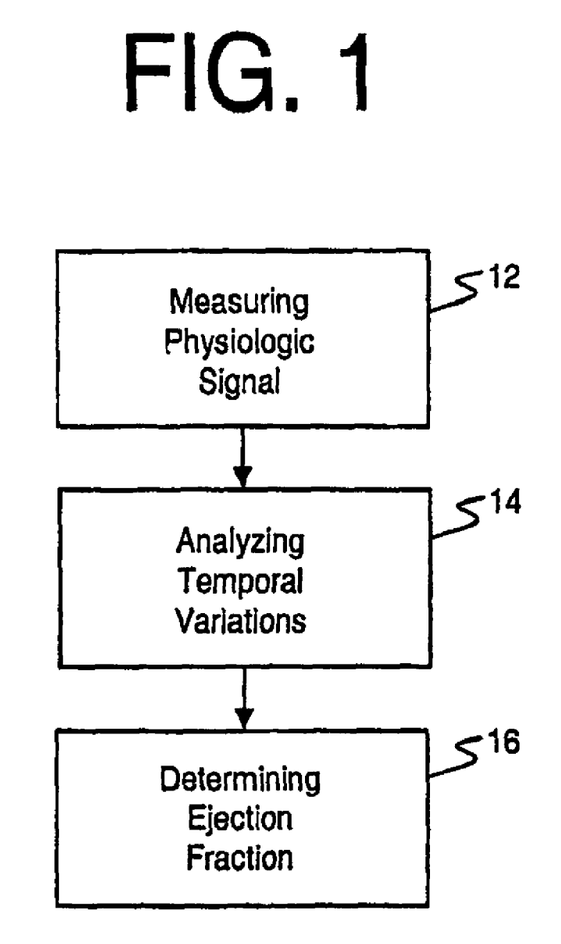
FIG. 1 is a flowchart illustrating an innovative technique for determining ejection fraction from a physiological signal indicative of blood pressure.

FIG. 1 illustrates an innovative technique for determining ejection fraction from a physiological signal indicative of blood pressure. This technique encompasses the recognition that there is significant information present in the variations of a blood pressure waveform or a related physiologic signal (e.g., photoplethysmography signal) over time, and that this information may be captured or extracted by mathematical analysis so as to determine ejection fraction as well as other important cardiovascular variables. Significant information is present in the temporal signal variations that occur within the systolic ejection phase of a beat or cardiac cycle, within a cardiac cycle, and from one cardiac cycle to another (i.e., what is commonly referred to as beat-to-beat variability). The technique therefore involves extracting this information by analyzing a blood pressure waveform or related physiologic signal at more than one of its time instances and then determining ejection fraction based in part on the extracted information. The extracted information may be obtained from within the systolic ejection phase of a cardiac cycle, from within a cardiac cycle, and/or from different cardiac cycles.

Figure 2:
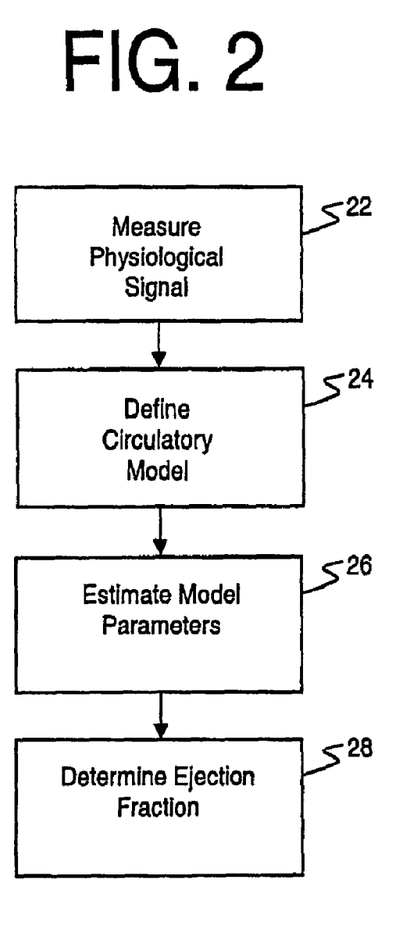
FIG. 2 is a flowchart illustrating a method for determining ejection fraction using a circulatory model.

With reference to FIG. 2, one exemplary embodiment of this technique involves the use of a circulatory model to estimate the parameters used to compute ejection fraction. Each step of this technique is further described below. However, it is understood that techniques which do not involve the use of a circulatory model are also contemplated by this disclosure.

A physiological signal is first measured as indicated at 22. The physiological signal is preferably a blood pressure waveform taken at any site in an arterial tree of a subject, including the systemic arteries, pulmonary artery, left ventricle or the right ventricle. Alternatively, the physiological signal could be related to a blood pressure waveform, such as a photoplethymograph signal. Other types of signals indicative of blood pressure are also contemplated by this disclosure.

Figure 3:
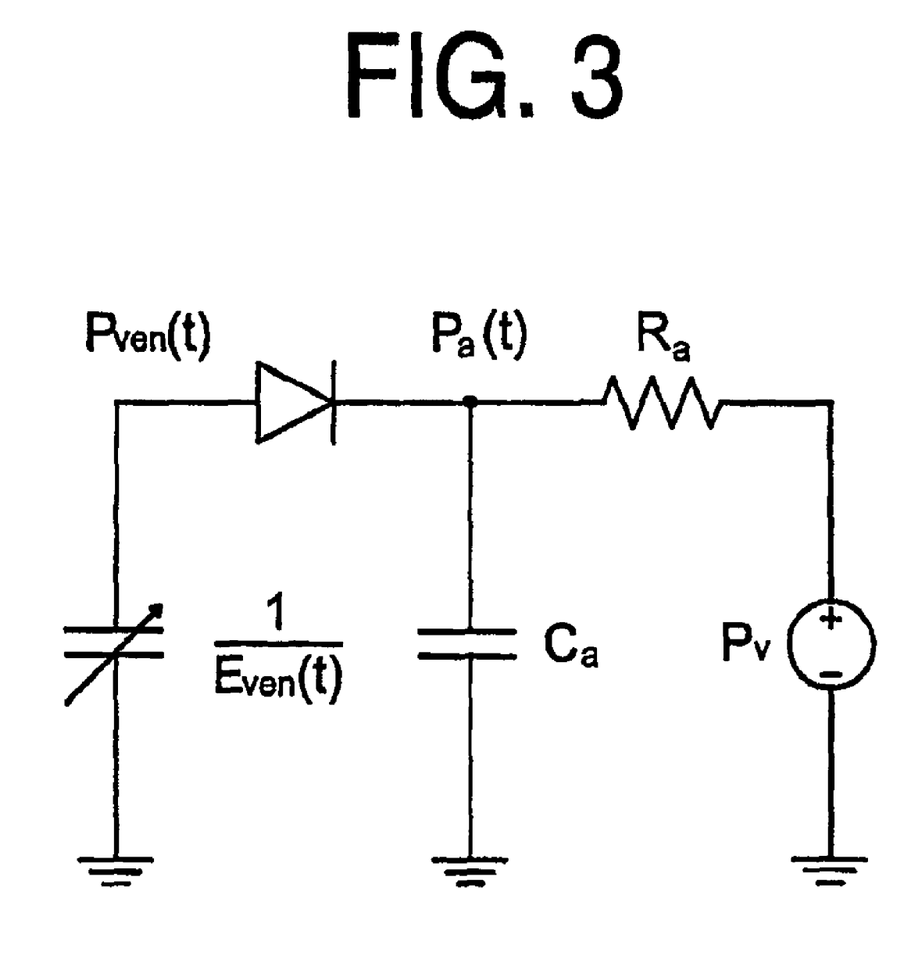
FIG. 3 is a diagram of an exemplary circulatory model.

Next, a circulatory model is defined at 24 to predict the physiological signal. In an exemplary embodiment, the circulatory model is a lumped parameter model in an electrical analog form, where voltage correlates to pressure (P), electric charge correlates to volume (v) and current correlates to flow rate. More specifically, the model embodies a ventricle (ven), a ventricular outflow valve, arteries (a), and veins (v) of either systemic or pulmonary circulation as shown in FIG. 3. In the exemplary model, the ventricle is represented with a variable elastance (E) (or capacitance (C=1/E)) model whose elastance oscillates over time (t) so as to drive the flow of blood in the model. The ventricular outflow valve is modeled by an ideal diode (with or without a resistance) in order to ensure uni-directional blood flow. The arteries are represented with a Windkessel model accounting for the volume storage capacity of the large arteries and the resistance (R) to flow of the small arteries. The veins are modeled by a pressure source or reservoir in the form of a constant voltage source. In addition to a capacitance, it is noted that the ventricle and large arteries are parameterized with an unstressed (0) volume (i.e., the filling volume at zero pressure). It is understood that the circulatory system may be represented using other types of models.

Key assumptions underlying the exemplary model are further described below. First, $C_a$ is constant over the course of days. For example, experimental data has indicated that the systemic arterial compliance (SAC) is approximately constant over a wide pressure range and on the time scale of months to years. The remaining model parameters (including $P_v$) are constant over the time interval of the mathematical analysis, which may range from the duration of the systolic ejection phase up to, e.g., 30-60 seconds (see below). For example, experimental data has shown that the local and autonomic nervous mechanisms responsible for modulating SAR are much slower than the heart rate, the LV pressure-volume relationship during systole is approximately linear over a wide pressure range, and the pulsatility of systemic venous pressure is small relative to SAP due to the systemic venous capacitance nominally being about 50 times greater than the SAC. During the systolic ejection phase, $P(t) = P_{ven}(t) = P_a(t)$. This equality is justified in subjects without stenosis of the ventricular outflow valve. Intrathoracic pressure, the actual external reference pressure of the heart-lung unit and thoracic arteries, is negligible with respect to $P_a(t)$. For example, the magnitude of average SAP is normally about 25 times larger than that of intrathoracic pressure The model parameters are then estimated at 26 from the measured physiological signal. For example, the model parameters may be estimated by fitting the circulatory model to the measured physiological signal. Continuing with the example set forth above, the dynamic equation governing the exemplary circulatory model during the systolic ejection phase is given as follows:

$$\frac{P(bs)}{C_a E_{ven}(bs)} - \frac{P(t)}{C_a E_{ven}(t)} = P(t) - P(bs) + \frac{1}{\tau}\int_{bs}^{t} P(\lambda)d\lambda - \frac{P_v(t-bs)}{\tau}, \quad (2)$$

$$bs < t \leq es,$$

where $\tau = R_a C_a$, while t=bs and t=es respectively denote the beginning and end of the systolic ejection phase. In order to estimate model parameters from a measured blood pressure waveform, this dynamic equation may be discretized. For example, the equation may be discretized by approximation of its integral via the trapezoidal formula as follows:

$$\frac{P(0)}{C_a E_{ven}(0)} - \frac{P(nT)}{C_a E_{ven}(nT)} = \quad (3)$$

$$P(nT) - P(0) + \frac{T}{2\tau}\sum_{k=1}^{n}(P(kT) + P((k-1)T)) - \frac{P_v nT}{\tau}, \quad 1 \leq n \leq N.$$

Here, T is the sampling period, n=0 corresponds to the first sample in the systolic ejection phase for which t>bs, and n=N corresponds to the last sample in the systolic ejection phase for which t≤es. T and the blood pressure samples $P(nT)$ for $0 \leq n \leq N$ are considered to be known (through measurement and sampling), while the proportional model parameters, $\tau$ and $C_a E_{ven}(nT)$ for $0 \leq n \leq N$, and the absolute model parameter $P_v$ are unknown. It is evident that equation (3) does not provide a basis for uniquely determining the unknown parameters from the known sampled blood pressure waveform, because it represents an underdetermined set of equations with N equations and N+3 unknowns.

Figure 4:
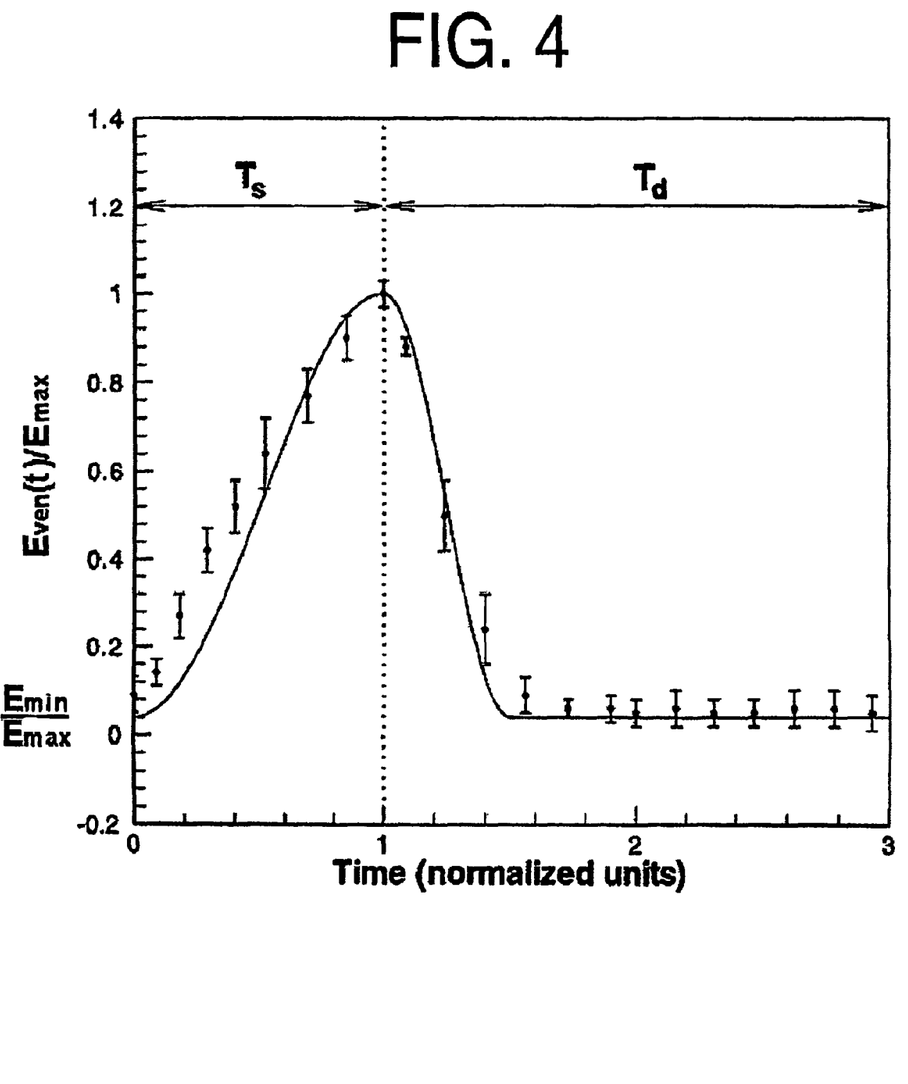
FIG. 4 is a graph depicting the time-vary ventricular elastance function.

Certain embodiments therefore assume a particular parametric function to succinctly characterize the temporal evolution of $E_{ven}(t)$ so as to result in a solvable (i.e., exactly determined or overdetermined) set of equations. This assumption is based on the compelling experimental and computational studies which are further described in articles by Senzaki et al entitled "Single-beat estimation of end-systolic pressure-volume relation in humans: a new method with the potential for noninvasive application" *Circulation*, 94:2497-2506, 1996 and by Heldt et al entitled "Computational modeling of cardiovascular response to orthostatic stress" *J. Appl. Physiol.*, 92(3):1239-1254, 2002 which are incorporated herein by reference. Senzaki et al specifically showed that experimentally measured, time-varying ventricular elastance functions, normalized both in amplitude and time, are remarkably consistent in 87 patients despite extremely wide variations in their ventricular state. Heldt et al subsequently demonstrated that these normalized experimental elastance data could be well represented, especially during the systolic ejection phase (i.e., the higher normalized elastance range), with the following parametric raised cosine function:

$$\frac{E_{ven}(t)}{E_{max}} = \quad (4)$$

$$\begin{cases} \frac{E_{min}}{E_{max}} + \frac{E_{max} - E_{min}}{2E_{max}} \cdot \left\{1 - \cos\left(\frac{\pi t}{T_s}\right)\right\}; & t_i \leq t < t_i + T_s \\ \frac{E_{min}}{E_{max}} + \frac{E_{max} - E_{min}}{2E_{max}} \cdot \left\{1 + \cos\left(\frac{2\pi(t - T_s)}{T_s}\right)\right\}, & t_i + T_s \leq t < t_i + \frac{3}{2}T_s \\ \frac{E_{min}}{E_{max}}, & t_i + \frac{3}{2}T_s \leq t < t_{i+1}, \end{cases}$$

where the subscript i denotes the beginning of the $i^{th}$ cardiac cycle, $E_{max}$ and $E_{min}$ are parameters respectively representing the maximum and minimum ventricular elastances over a cardiac cycle, and $T_s$ is a parameter indicating the time duration to reach $E_{max}$ from $E_{min}$ as shown in FIG. 4.

Substituting Equation (4) into Equation (3) results in N equations and six unknowns ($P_v$, $\tau$, $C_a E_{max}$, $C_a E_{min}$, $C_a E_{ven}(0)$, and $T_s$). As long as N≧6, then, in principle, these six parameters may be estimated from the sampled blood pressure waveform. The number of unknown parameters may be decreased by, for example, directly measuring $3T_s/2$ through the QT interval (assuming that the electromechanical ventricular contraction and relaxation delays are equivalent) and/or further assuming that $E_{min}/E_{max}$ is constant (equal to, e.g., ~0.05 as indicated in FIG. 4). Note that estimation of $C_a E_{min}$ is likely to be unreliable in this particular context, as it would essentially be based on an extrapolation. That is, $E_{min}$ is not directly "seen" during the systolic ejection phase. The number of unknown parameters may also be increased by, for example, letting the $3T_s/2$ term in Equation (4), which is related to the time duration to reach $E_{min}$ from $E_{max}$, be variable (e.g., ranging from $5T_s/4$ to $7T_s/4$). In general, increasing the number of parameters to characterize the time-varying ventricular elastance function will reduce the bias in the subsequent model parameter estimation at the expense of degrading the precision. Conversely, decreasing the number of parameters to characterize the time-varying ventricular elastance function will improve the precision of the subsequent model parameter estimation while perhaps only modestly increasing the bias. Also note that other types of parametric functions may be utilized to represent the time-varying ventricular elastance function (e.g., a Gaussian function). Additionally, other types of restrictions on $E_{ven}(t)$ may be assumed (e.g., it has a zero derivative during the systolic ejection phase) in order to arrive at a solvable set of equations.

Lastly, ejection fraction is determined at 28 using the estimated model parameters and the physiological signal. An absolute ejection fraction may be computed using the following equation:

$$EF = \frac{\frac{SV}{C_a}}{\frac{EDV}{C_a}} = \frac{\frac{EDV}{C_a} - \frac{ESV}{C_a}}{\frac{EDV}{C_a}} = \frac{\frac{P(0)}{C_a E_{ven}(0)} - \frac{P(NT)}{C_a E_{ven}(NT)}}{\frac{P(0)}{C_a E_{ven}(0)} + \frac{V_{ven,0}}{C_a}}. \quad (5)$$

In the exemplary embodiment, the ventricular elastance function is proportionally estimated by solving equation 3 in the manner described above. Note that $V_{ven,0}/C_a$ in this equation, which represents proportional, unstressed ventricular volume, generally cannot be estimated from the sampled blood pressure waveform. However, this parameter is normally much smaller than $EDV/C_a$ (e.g., about a magnitude smaller). Thus, $V_{ven,0}/C_a$ may be assumed to be zero or equal to a nominal value (e.g., 5-15 mmHg in dogs and humans) so as to reduce any bias in the resulting EF estimate. Also note that a nominal value of intrathoracic pressure (e.g., -4 mmHg during spontaneous breathing) may be subtracted from P(t) in Equation (5) to further refine the EF estimate. Alternatively, $V_{ven,0}/C_a$ may be measured by first obtaining a single, independent measurement of EF through, for example, an imaging technique and then finding the value of $V_{ven,0}/C_a$ that makes the EF estimated from the sampled blood pressure waveform equivalent to the independent EF measurement. In this case, the value determined for $V_{ven,0}/C_a$ may be utilized to compute subsequent EF estimates by blood pressure waveform analysis, where large changes in these EF estimates over time may, in turn, suggest when to re-image the heart. This alternative approach may be preferred in patients with dilated cardiomyopathy. It is also possible that the ratio of SV to stressed EDV (i.e., $V_{ven,0}/C_a=0$) could be a more valuable indicator of global ventricular function.

Aside from ejection fraction, other important cardiovascular variables may also be determined from the estimated model parameters. Exemplary variables include proportional stroke volume through a numerator term of Equation (5), proportional arterial resistance $R_a$ through $\tau$, proportional maximum ventricular elastance $E_{max}$, which is known to be a relatively specific index of global ventricular contractility, and absolute venous pressure through $P_v$. Other cardiovascular variable are also contemplated by this disclosure.

The exemplary method for determining ejection fraction may be tailored according to the particular blood pressure waveform available for analysis. For example, the lumped parameter circulatory model of FIG. 3 is known to be a good mathematical representation of systemic arterial pressure (SAP) waveforms measured centrally in the aorta in which the confounding effects of distributed wave phenomena are relatively small. Thus, certain embodiments of the invention fit this model directly to a measured central SAP waveform. In exemplary embodiments, $P_v$ is assumed to be zero a priori as justified by the relatively large SAR and systemic venous compliance. In other exemplary embodiments, the ventricular parameters to be estimated are $C_a E_{max}$, $C_a E_{ven}(0)$, and $T_s$ or $C_a E_{max} C_a E_{ven}(0)$ when a surface ECG is also available for directly measuring or approximating $T_s$ (i.e., $E_{min}/E_{max}$ is set to a constant value).

In certain embodiments, Equations (3) and (4) are fitted to the systolic ejection intervals of the central SAP waveform in order to estimate the unknown parameters on a beat-to-beat basis. The systolic ejection intervals may be determined by various known methods. For example, the beginning of the systolic ejection phase (t=bs) may be established as the onset of upstroke of the central SAP pulse, while the end of the systolic ejection phase (t=es) may be determined through the dicrotic notch (i.e., incisura) denoting aortic valve closure. Alternatively, the systolic ejection phase may be approximated through any empirical formula based on the cardiac cycle length (see, Malik, M. If Dr. Bazett had had a computer . . . *PACE*, 19(1):1635-1639, 1996) or other physiologic signals such as a phonocardiogram. Moreover, the data fitting procedure may be performed by various known techniques such as nonlinear least squares via a brute force search over a physiologic range of parameter values or, more efficiently, via Newton's methods.

In one preferred embodiment, the parameter estimation procedure is conducted on a beat-to-beat basis in two steps. In the first step, $\tau$ is estimated from the diastolic intervals (i.e., the intervals not corresponding to the systolic ejection phase intervals) of the central SAP waveform. For example, according to the model of FIG. 3, SAP should decay like a pure exponential during each diastolic interval with a time constant equal to $\tau$. Thus, in certain embodiments, $\tau$ is determined by directly fitting a mono-exponential function to the diastolic SAP interval (or any portion of it) based on the following equation:

$$P(t) = Ae^{-t/\tau} + w(t). \quad (6)$$

The parameters A and $\tau$ may be estimated according to any procedure known in the art. For example, the parameters may be determined by the closed form, linear least squares solution after log transformation of P(t). Alternatively, if $P_v$ is not assumed to be zero, then $\tau$ and $P_v$ may be determined by directly fitting a mono-exponential function plus a constant term to the diastolic SAP interval (or any portion of it), where the estimated constant term represents $P_v$. In the second step, the estimated values of $\tau$ (and $P_v$) are plugged into Equations (3) and (4), and the remaining ventricular model parameters are estimated as described above.

In other embodiments, absolute LVEF is computed for each beat from the estimated proportional ventricular parameters and the measured central SAP waveform according to Equation (5). In addition, other important cardiovascular variables such as proportional, beat-to-beat SV and proportional, beat-to-beat SAR are determined as described above. In certain embodiments, the proportional cardiovascular variables are calibrated to absolute values using a nomogram or a single absolute measurement of SV via, e.g., cardiac imaging or bolus thermodilution. In certain embodiments, the beat-to-beat estimates are averaged over any number of beats to further reduce the estimation error (but at the expense of the temporal resolution of the estimated cardiovascular variables).

Embodiments as applied to central SAP waveforms may be used, e.g., in conjunction with implanted devices for ambulatory monitoring, in animal research, as well as in any clinical setting in which an aortic pressure catheter has been installed.

Certain embodiments apply the methods described above for a central SAP waveform to a SAP waveform measured at any peripheral site in the systemic arterial tree (e.g., radial artery, femoral artery, carotid artery). However, it is recognized that peripheral SAP waveforms are heavily complicated by distributed wave phenomena over time scales within a cardiac cycle. So, for example, the diastolic intervals of a peripheral SAP waveform usually do not appear as pure exponential decays. Thus, the measured peripheral SAP waveform(s) are first mathematically transformed into a central SAP waveform and then the methods described above for a central SAP waveform are applied to the "predicted" or "reconstructed" central SAP waveform.

The mathematical transformation from peripheral SAP to central SAP may be performed by various known methods. For instance, the generalized transfer function or model-based transfer function approach is employed in which both peripheral and central SAP waveforms are initially measured, an individualized or group-averaged transfer function is estimated relating the measured waveforms, and then this transfer function estimate is subsequently applied to a measured peripheral SAP waveform in order to predict the unmeasured central SAP waveform. In preferred embodiments, mathematical transformation techniques that are entirely data-dependent are utilized such as blind system identification (with channel dynamics assumed to be unity gain), which requires two or more peripheral SAP waveforms to predict the central SAP waveform.

Embodiments as applied to peripheral SAP waveforms may be used, e.g., for monitoring in the ICU, OR, and recovery room based on invasive catheter systems or for monitoring at home or in the ER in conjunction with non-invasive SAP systems.

Since left ventricle pressure (LVP) is assumed to be equal to central SAP during the systolic ejection phase (see above), the methods described above for a central SAP waveform generally apply to the LVP waveform as well. However, methods for identifying the systolic ejection phase intervals of the pressure waveform and determining τ (and, if desired, $P_v$) in the two-step estimation procedure must be different, because LVP is substantially different from central SAP during the diastolic interval. That is, in certain embodiments, the beginning of the systolic ejection phase (t=bs) may be established as the time in which the maximum derivative of LVP occurs within the cardiac cycle, while the end of the systolic ejection phase (t=es) may be determined as the time in which LVP reaches a maximum within the cardiac cycle. Other method for identifying the systolic ejection phase as note above may be utilized. In certain embodiments of a two-step parameter estimation procedure, τ (and possibly $P_v$) are estimated from consecutive systolic ejection phase intervals spanning over, e.g., 30-60 seconds of the LVP waveform. Further details regarding this estimation technique may be found in found in U.S. patent application Ser. No. 11/358,379 entitled "Methods and apparatus for Determining Cardiac Output and Left Arterial Pressure" which was filed on Feb. 21, 2006 and is incorporated herein by reference. Then, in the second step, the estimated values of τ (and $P_v$) are plugged into Equations (3) and (4), and the remaining ventricular model parameters are estimated from the same systolic ejection phase intervals of the LVP waveform used to calculate τ (and possibly $P_v$) as described above.

Embodiments as applied to LVP waveforms may be used, e.g., in conjunction with implanted devices for ambulatory monitoring, in animal research, as well as in any clinical setting in which an LVP catheter has been installed.

In certain embodiments, the lumped parameter circulatory model of FIG. 3 is assumed to be a good representation of a PAP waveform. Thus, the methods for estimating the model parameters from a central SAP waveform are applied to a PAP waveform. However, in preferred embodiments, $P_v$ is not assumed to be zero due to the relatively small pulmonary arterial resistance (PAR). It is recognized that PAP waveforms are often complicated as a result of inertial effects and distributed wave phenomena. Thus, preferred embodiments account for these more complex dynamics, which are not captured by the lumped parameter circulatory model of FIG. 3. In certain embodiments, more complex lumped parameter models such as that described by Urzua et al in "Estimation of ventricular volume and elastance from the arterial pressure waveform" *J. Clin. Monit. Comput.*, 14:177-181, 1998 are utilized to represent the PAP waveform, and the chosen model is then similarly fitted to the measured PAP waveform in order to estimate its parameters.

In certain embodiments, RVEF is computed for each beat from the estimated proportional ventricular parameters and the measured PAP waveform according to Equation (5). In addition, other important cardiovascular variables such as proportional, beat-to-beat SV, proportional, beat-to-beat PAR, and absolute left atrial pressure (LAP through $P_v$ as the resistance between the pulmonary veins and left atrium is very small) are determined as described above. In certain embodiments, the proportional cardiovascular variables are calibrated to absolute values using a nomogram or a single absolute measurement of SV via, e.g., cardiac imaging or bolus thermodilution. In certain embodiments, the beat-to-beat estimates are averaged over any number of beats to further reduce the estimation error.

Embodiments as applied to PAP waveforms may be used, e.g., for monitoring in the ICU, OR, and recovery room and in conjunction with implanted devices for ambulatory monitoring.

In certain embodiments, the methods for LVP waveforms are applied to an RVP waveform. However, $P_v$ is not assumed to be zero in these embodiments, and the resulting estimated cardiovascular variables correspond to those determined from the PAP waveform (e.g., RVEF, proportional SV, LAP). Embodiments as applied to RVP waveforms may be used, e.g., in conjunction with implanted devices for ambulatory monitoring.

Figure 5:
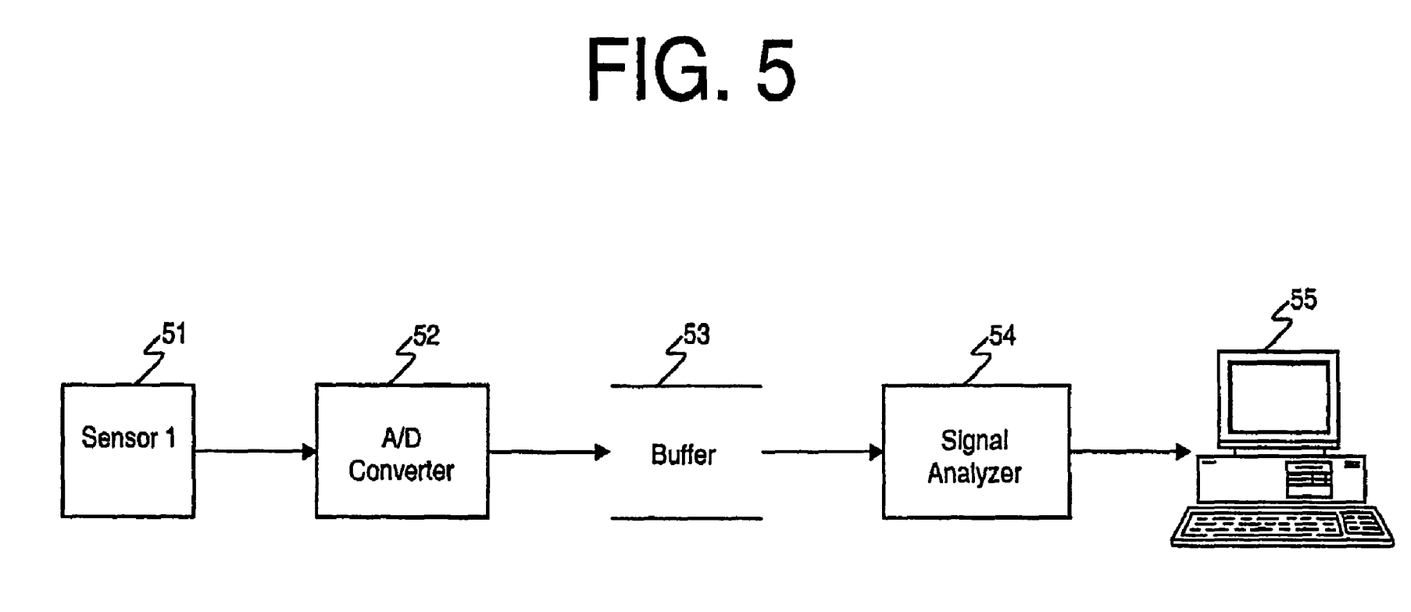
FIG. 5 is a diagram of an exemplary apparatus for implementing the method of this disclosure.

FIG. 5 illustrates an exemplary apparatus 50 for implementing the methods described above. One or more sensor 51 measure a physiological signal indicative of blood pressure in a subject. Other physiologic signals, such as surface ECGs and a phonocardiogram, may also be input into the apparatus. These signals may be acquired using standard methods and instruments such as those mentioned above. As they are being measured, the signals are fed into a corresponding analog-to-digital converter 52 and then stored in a buffer system 53. The most recent time intervals of the sampled signals (e.g., one cardiac cycle to 30-60 seconds) are transferred from the buffer system to a signal analyzer 54 (i.e., processing unit), which analyzes the signals according to the methods described above. The buffer and processing unit may be implemented using, for example, any standard microcomputer or implanted circulatory monitoring device running appropriate software to implement the mathematical operations described above. It is to be understood that only the relevant steps of the methodology are discussed above, but that other software-implemented instructions may be needed to control and manage the overall operation of the system. The software components may be coded in any suitable programming language and may be embodied in any of a range of computer-readable media including, but not limited to, floppy disks, hard disks, CDs, zip disks, and DVD disks. Outputs such as LVEF, proportional SV, and proportional SAR or RVEF, proportional SV, proportional PAR, and LAP may be illustrated on a visual display such as a computer screen and/or may be printed or transmitted to a remote location. The circulatory signals themselves, and analysis thereof, may also be displayed. In a preferred embodiment of the system, the process is continuously repeated thereby providing the on-line monitoring of LVEF, proportional SV, and proportional SAR; RVEF, proportional SV, proportional PAR, and LAP;

and/or other hemodynamic variables (with a delay equal to half the selected analysis interval). Alternatively or additionally, absolute SV and SAR or PAR may be computed and displayed through a nomogram or a single, independent measurement of absolute SV. In certain embodiments of the invention, an alarm is triggered upon excessive changes in any of the estimated variables. Finally, the methods may further comprise the step of administering therapy to the subject, or modifying the subject's therapy, based on one or more hemodynamic variables obtained according to the methods and apparatus of the invention.

The above description is merely exemplary in nature and is not intended to limit the present disclosure, application, or uses.

What is claimed is:

1. A method for determining ejection fraction comprising:
   measuring a blood pressure signal of a patient;
   defining a circulatory model for predicting the blood pressure signal;
   estimating parameters of the circulatory model only from the blood pressure signal; and
   determining ejection fraction only from the estimated model parameters and the blood pressure signal.

2. The method of claim 1 wherein the circulatory model represents a ventricle, a ventricular outflow valve, arteries, and veins.

3. The method of claim 2 wherein the ventricle is represented with a time-varying elastance model.

4. The method of claim 3 wherein the time-varying elastance model is characterized with a parametric function.

5. The method of claim 4 wherein the parametric function is a raised cosine function or a Gaussian function.

6. The method of claim 4 wherein the parameters of the parametric function include maximum ventricular elastance, minimum ventricular elastance, a time it takes to reach the maximum ventricular elastance from the minimum ventricular elastance, and a value of the ventricular elastance when the systolic ejection phase begins.

7. The method of claim 6 wherein the minimum ventricular elastance is set to a constant fraction of the maximum ventricular elastance.

8. The method of claim 3 wherein ejection fraction is computed based on the time-varying ventricular elastance model, the estimated model parameters, and the measured blood pressure signal.

9. The method of claim 8 wherein an absolute ejection fraction is obtained by cancellation of an arterial compliance scale factor.

10. The method of claim 8 wherein the time-varying ventricular elastance model includes a term related to unstressed volume, which is assumed to be zero or a nominal value.

11. The method of claim 8 wherein the time-varying ventricular elastance model includes a term related to unstressed volume, which is determined with an independent measure of ejection fraction or ventricular volume.

12. The method of claim 11 wherein the term related to unstressed volume is utilized to compute subsequent values of ejection fraction.

13. The method of claim 2 wherein the arteries are represented with a lumped parameter model.

14. The method of claim 13 wherein the lumped parameter model is the Windkessel model, which is governed by a single time constant equal to a product of the total peripheral resistance and arterial compliance.

15. The method of claim 2 wherein the veins are represented with a constant voltage source.

16. The method of claim 15 wherein the voltage source is set to zero.

17. The method of claim 1 further comprising signal processing prior to estimating the model parameters so as to suppress wave and inertial effects in the blood pressure signal.

18. The method of claim 17 wherein the wave and inertial effects are suppressed by applying generalized transfer function methods to the measured blood pressure signal or by applying multi-channel blind system identification methods to the measured blood pressure signals.

19. The method of claim 1 wherein at least one model parameters is estimated to within a proportionality constant equal to arterial compliance.

20. The method of claim 1 wherein the model parameters are estimated by fitting the parameters of the circulatory model to the measured blood pressure signal.

21. The method of claim 20 wherein the parameters are fitted over a systolic ejection phase of a cardiac cycle.

22. The method of claim 21 wherein the systolic ejection phase is determined through a dicrotic notch, empirical formula involving cardiac cycle length, or a phonocardiogram.

23. The method of claim 20 wherein the model parameters characterizing the arteries and veins are estimated by fitting the parameters over at least a portion of a diastolic phase of a cardiac cycle and then estimating parameters representing the ventricle and the ventricular outflow valve are estimated by fitting the parameters over a preceding systolic ejection phase.

24. The method of claim 23 wherein a parameter characterizing the arteries is a Windkessel time constant.

25. The method of claim 24 wherein the Windkessel time constant is estimated by fitting a mono-exponential function to at least part of a diastolic phase of a cardiac cycle.

26. The method of claim 23 wherein the parameters characterizing the arteries and veins are respectively a Windkessel time constant and a constant pressure term.

27. The method of claim 26 wherein the Windkessel time constant and constant pressure term are estimated by fitting a mono-exponential function to at least a portion of the diastolic phase of the cardiac cycle.

28. The method of claim 20 wherein the parameters characterizing the arteries and veins are estimated by fitting these parameters over a time interval greater than a cardiac cycle and then estimating the parameters representing the ventricle and ventricular outflow valve are estimated by fitting these parameters over a systolic ejection phase of a cardiac cycle within the same time interval.

29. The method of claim 1 further comprising the determination of a cardiovascular variable other than ejection fraction to within a proportionality constant.

30. A method for determining ejection fraction comprising steps of:
   measuring a blood pressure signal of a patient;
   defining a circulatory model for predicting the blood pressure signal;
   estimating parameters of the circulatory model, to within a proportionality constant, using only the blood pressure signal; and
   computing absolute ejection fraction only from the estimated proportional model parameters and the blood pressure signal through cancellation of the proportionality constant.

31. The method of claim 30 wherein the circulatory model represents a ventricle, a ventricular outflow valve, arteries, and veins.

32. The method of claim 31 wherein the ventricle is represented with a time-varying elastance model.

33. The method of claim 32 wherein the time-varying elastance model is characterized with a parametric function.

34. The method of claim 33 wherein the parametric function is a raised cosine function or a Gaussian function.

35. The method of claim 33 wherein the parameters of the parametric function include maximum ventricular elastance, minimum ventricular elastance, a time it takes to reach the maximum ventricular elastance from the minimum ventricular elastance, and a value of the ventricular elastance when the systolic ejection phase begins.

36. The method of claim 35 wherein the minimum ventricular elastance is set to a constant fraction of the maximum ventricular elastance.

37. The method of claim 32 wherein absolute ejection fraction is computed based on the time-varying ventricular elastance model, the estimated proportional model parameters, and the measured blood pressure signal.

38. The method of claim 37 wherein the time-varying ventricular elastance model includes a term related to proportional unstressed volume, which is assumed to be zero or a nominal value.

39. The method of claim 37 wherein the time-varying ventricular elastance model includes a term related to proportional unstressed volume, which is determined with an independent measure of ejection fraction or ventricular volume.

40. The method of claim 37 wherein the determined term related to unstressed volume is utilized to compute subsequent values of ejection fraction.

41. The method of claim 31 wherein the arteries are represented with a lumped parameter model.

42. The method of claim 41 wherein the lumped parameter model is a Windkessel model, which is governed by a single time constant equal to a product of a total peripheral resistance and arterial compliance.

43. The method of claim 31 wherein the veins are represented with a constant voltage source.

44. The method of claim 43 wherein the voltage source is set to zero.

45. The method of claim 30 further comprising signal processing prior to estimating the model parameters so as to suppress wave and inertial effects in the blood pressure signal.

46. The method of claim 45 wherein the wave and inertial effects are suppressed by applying generalized transfer function methods to the measured blood pressure signal or by applying multi-channel blind system identification methods to the measured physiologic signals.

47. The method of claim 30 wherein the proportionality constant is arterial compliance.

48. The method of claim 30 wherein the model parameters are estimated by fitting the parameters of the circulatory model to the measured blood pressure signal.

49. The method of claim 48 wherein the model parameters are fitted over a systolic ejection phase of a cardiac cycle.

50. The method of claim 49 wherein the systolic ejection phase is determined through dicrotic notch, empirical formula involving cardiac cycle length, or a phonocardiogram.

51. The method of claim 48 wherein the model parameters characterizing the arteries and veins are estimated by fitting the parameters over at least a portion of a diastolic phase of a cardiac cycle and estimating the parameters representing the ventricle and ventricular outflow valve by fitting the parameters over a preceding systolic ejection phase.

52. The method of claim 51 wherein a parameter characterizing the arteries is a Windkessel time constant.

53. The method of claim 52 wherein the Windkessel time constant is estimated by fitting a mono-exponential function to at least a portion of the diastolic phase of a cardiac cycle.

54. The method of claim 51 wherein the parameters characterizing the arteries and veins are respectively a Windkessel time constant and a constant pressure term.

55. The method of claim 54 wherein the Windkessel time constant and constant pressure term are estimated by fitting a mono-exponential function to part of the diastolic phase of a cardiac cycle.

56. The method of claim 48 wherein the parameters characterizing the arteries and veins are estimated by fitting these parameters over a time interval greater than a cardiac cycle and then estimating the parameters representing the ventricle and ventricular outflow valve by fitting these parameters over a systolic ejection phase of a cardiac cycle within the same time interval.

57. The method of claim 30 further comprising the determination of a cardiovascular variable other than ejection fraction to within a proportionality constant.

* * * * *